United States Patent [19]

Mausner

[11] Patent Number: 5,658,580
[45] Date of Patent: Aug. 19, 1997

[54] SKIN CREAM COMPOSITION

[75] Inventor: Jack Mausner, New York, N.Y.

[73] Assignee: Chanel, Inc., Piscataway, N.J.

[21] Appl. No.: 539,349

[22] Filed: Oct. 5, 1995

Related U.S. Application Data

[63] Continuation-in-part of Ser. No. 118,962, Sep. 9, 1993, abandoned.

[51] Int. Cl.$^6$ ...................................................... A61K 7/48
[52] U.S. Cl. ........................... 424/401; 514/844; 514/847
[58] Field of Search ........................... 424/401; 514/844, 514/847

[56] References Cited

U.S. PATENT DOCUMENTS

| | | | |
|---|---|---|---|
| 3,697,643 | 10/1972 | Shepherd et al. | 424/63 |
| 3,864,275 | 2/1975 | Kan et al. | 252/316 |
| 3,911,105 | 10/1975 | Papantoniou et al. | 424/64 |
| 3,966,398 | 6/1976 | Vanlerberghe et al. | 8/11 |
| 4,125,549 | 11/1978 | Coopersmith et al. | 260/425 |
| 4,247,411 | 1/1981 | Vanlerberghe et al. | 252/316 |
| 4,369,037 | 1/1983 | Matsunaga et al. | 8/127.51 |
| 4,400,295 | 8/1983 | Ootsu et al. | 252/356 |
| 4,423,031 | 12/1983 | Murui et al. | 424/63 |
| 4,460,371 | 7/1984 | Abber | 604/897 |
| 4,481,186 | 11/1984 | Deckner | 424/59 |
| 4,549,990 | 10/1985 | Seguin et al. | 260/397.25 |
| 4,574,082 | 3/1986 | Tietjen et al. | 424/63 |
| 4,608,392 | 8/1986 | Jacquet et al. | 514/844 |
| 4,752,496 | 6/1988 | Fellows et al. | 427/27 |
| 4,758,599 | 7/1988 | Minetti | 424/63 |
| 4,820,510 | 4/1989 | Arraudeau et al. | 424/63 |
| 4,883,659 | 11/1989 | Goodman et al. | 424/68 |
| 4,925,667 | 5/1990 | Fellows et al. | 424/401 |
| 4,927,952 | 5/1990 | Gueyne et al. | 556/419 |
| 4,952,560 | 8/1990 | Kigasawa et al. | 514/2 |
| 4,980,155 | 12/1990 | Shah et al. | 424/63 |
| 4,988,502 | 1/1991 | Ounanian et al. | 424/63 |
| 5,034,226 | 7/1991 | Beck | 424/195.1 |
| 5,037,803 | 8/1991 | Gueyne et al. | 424/63 |
| 5,053,220 | 10/1991 | Arraudeau et al. | 424/63 |
| 5,053,221 | 10/1991 | Robertson et al. | 424/63 |
| 5,061,481 | 10/1991 | Suzuki et al. | 424/63 |
| 5,093,109 | 3/1992 | Mausner | 424/63 |
| 5,116,607 | 5/1992 | Jones | 424/70 |
| 5,182,103 | 1/1993 | Nakane et al. | 424/78.03 |
| 5,215,759 | 6/1993 | Mausner | 424/401 |
| 5,254,331 | 10/1993 | Mausner | 424/489 |
| 5,352,441 | 10/1994 | Mausner | 424/59 |
| 5,391,373 | 2/1995 | Mausner | 424/401 |

*Primary Examiner*—Jyothsna Venkat
*Attorney, Agent, or Firm*—Merchant, Gould, Smith, Edell, Welter & Schmidt

[57] ABSTRACT

A skin cream composition according to the present invention provides significant retexturization of the skin, producing significantly improved smoothness, as well as significantly minimizing age spots and improving color of the skin, together with increasing the firmness and moisture content of the skin. The composition also reduces the extent of sebum and/or oil on the skin. The composition can comprise: water, and emulsified and dispersed in the water: (1) sodium lactate; (2) a long-chain fatty acid ester of ascorbic acid; (3) a short-chain carboxylic acid ester of tocopherol; (4) witch hazel; and (5) horsetail extract. The sodium lactate, the ascorbic acid ester, the tocopherol ester, the witch hazel, and the horsetail extract are each present in a quantity sufficient to increase the smoothness and/or firmness and to diminish the oiliness of skin to which the composition is applied. The composition can also contain an active metabolite complex of polysaccharides and peptides extracted from a bacterial culture medium as an additional, optional, cosmetic component. The composition can also comprise additional, ancillary, components.

15 Claims, No Drawings

SKIN CREAM COMPOSITION

CROSS-REFERENCE

This application is a continuation-in-part application of U.S. application Ser. No. 08/118,962, by Jack Mausner, filed Sep. 9, 1993 now abandoned and entitled "Metabolite-Containing Skin Cream Composition."

BACKGROUND

This invention is directed to an improved skin cream composition.

Modern environmental conditions, such as heating and air conditioning, exposure to the sun and environmental pollution, exert severe stress on the skin and accelerate the natural aging process, resulting in wrinkles, loss of firmness and elasticity, age spots, discoloration, dryness, and other cosmetically undesirable effects. Additionally, for many people with oily skin, skin problems are exacerbated by the excessive oil content, causing overproduction of sebum. Although a number of skin cream compositions already exist, there is a need for a simple-to-apply and effective cosmetic treatment, such as a skin cream, that can retexturize the skin, increase its firmness, color, and smoothness, while increasing its moisture content to overcome drying caused by the environment. Additionally, there is a need for a cosmetic composition that can provide these advantages while reducing the amount of oil and sebum on the skin of people with oily skin.

SUMMARY

I have developed a skin cream composition incorporating a new combination of ingredients. The skin cream composition of the present invention simultaneously promotes significant retexturizing of the skin, significantly increasing its smoothness, improving its color, while also increasing its firmness and moisture content. The skin cream composition is particularly effective with oily skin, reducing the amount of oil and/or sebum deposited on the skin.

In general, a skin cream composition according to the present invention comprises: water, and emulsified and dispersed in the water:

(1) sodium lactate;

(2) a long-chain fatty acid ester of ascorbic acid;

(3) a short-chain carboxylic acid ester of tocopherol;

(4) witch hazel; and (5) horsetail extract.

The sodium lactate, the ascorbic acid ester, the tocopherol ester, the witch hazel, and the horsetail extract are each present in a quantity sufficient to increase the smoothness and/or firmness and to diminish the oiliness of skin to which the composition is applied. These ingredients comprise the cosmetic components.

Preferably, the sodium lactate comprises from about 4.25% to about 5.75% of the composition, the ascorbic acid ester comprises from about 0.01% to about 0.03% of the composition, the tocopherol ester comprises from about 0,001% to about 0.02% of the composition, the witch hazel comprises from about 6.8% to about 9.2% of the composition, and the horsetail extract comprises from about 0.02% to about 0.1% of the composition.

Preferably, the long-chain fatty acid ester of ascorbic acid is selected from the group consisting of ascorbyl palmitate, ascorbyl myristate, and ascorbyl stearate. Most preferably, the long-chain fatty acid ester of ascorbic acid is ascorbyl palmitate.

Preferably, the tocopherol ester of a short-chain fatty acid is selected from the group consisting of tocopheryl acetate and tocopheryl propionate. Most preferably, the tocopherol ester is tocopherol acetate.

An optional cosmetic component in the skin cream composition is an active metabolite complex of polysaccharides and peptides extracted from a bacterial culture medium, which can comprise from about 5.1% to about 6.9% of the composition.

The skin cream composition of the present invention can further comprise additional, ancillary components whose use is optional but preferable. These ancillary components comprise:

(1) a thickener component;

(2) a preservative component;

(3) a lipid-soluble component;

(4) a methoxycinnamate ester of a medium-chain alcohol;

(5) benzophenone-3;

(6) fragrance;

(7) a complex consisting essentially of polyacrylamide, $C_{13}$–$C_{14}$ isoparaffin, laureth-7, and water; and (8) coloring.

Preferably, the composition of the present invention comprises all of these ancillary components.

The thickener component can comprise at least one of xanthan gum and carrageenan. Preferably, the thickener component comprises both xanthan gum and carrageenan, and the xanthan gum comprises from about 0.05% to about 0.15% of the composition and the carrageenan comprises from about 0.05% to about 0.15% of the composition.

The preservative component can comprise at least one of:

(a) a complex of propylene glycol, phenoxyethanol, chlorphenesin, and methylparaben;

(b) methylparaben;

(c) butylparaben; and (d) propylparaben.

Preferably, the preservative component comprises all four of these ingredients, and the complex of propylene glycol, phenoxyethanol, chlorphenesin, and methylparaben comprises from about 1.9% to about 2.6% of the composition, the methylparaben comprises from about 0.05% to about 0.15% of the composition, the butylparaben comprises from about 0.02% to about 0.1% of the composition, and the propylparaben comprises from about 0.02% to about 0.1% of the composition.

The lipid-soluble component can comprise at least one ingredient selected from the group consisting of:

(i) steareth-2;

(ii) steareth-21;

(iii) a neopentanoate ester of a branched-chain alcohol selected from the group consisting of octyldodecyl neopentanoate, heptyldodecyl neopentanoate, nonyldodecyl neopentanoate, octylundecyl neopentanoate, heptylundecyl neopentanoate, nonylundecyl neopentanoate, octyltridecyl neopentanoate, heptyltridecyl neopentanoate, and nonyltridecyl neopentanoate; and (iv) dimethicone.

Preferably, the lipid-soluble components comprises steareth-2, steareth-21, octyldodecyl neopentanoate, and dimethicone, and wherein the steareth-2 comprises from about 0.85% to about 1.15% of the composition, the steareth-21 comprises from about 0.85% to about 1.15% of the composition, the octyldodecyl neopentanoate comprises from about 1.25% to about 1.75% of the composition, and the dimethicone comprises from about 0.4% to about 0.6% of the composition.

Preferably, the composition further comprises a methoxycinnamate ester of a medium-chain alcohol selected from the group consisting of octyl methoxycinnamate, heptyl methoxycinnamate, and nonyl methoxycinnamate. Preferably, the methoxycinnamate ester of the medium-chain alcohol is octyl methoxycinnamate, and the octyl methoxycinnamate comprises from about 3.4% to about 4.6% of the composition.

Preferably, the benzophenone-3 comprises from about 1.7% to about 2.3% of the composition.

Preferably, the fragrance comprises from about 0.3% to about 0.4% of the composition.

Preferably, the composition further comprises a complex consisting essentially of polyacrylamide, $C_{13}$–$C_{14}$ isoparaffin, laureth-7, and water, wherein the polyacrylamide comprises from about 49.6% to about 63.8% of the complex, the $C_{13}$–$C_{14}$ isoparaffin comprises from about 21.3% to about 35.5% of the complex, the laureth-7 comprises from about 4.2% to about 11.3% of the complex, and the water comprises from about 4.2% to about 9.9% of the complex. Most preferably, the complex of polyacrylamide, $C_{13}$–$C_{14}$ isoparaffin, laureth-7 and water comprises from about 4.25% to about 5.75% of the composition.

Preferably, the coloring agent is FD&C Blue#1, and the coloring agent comprises from about 0.0001% to about 0.1% of the composition.

A preferred skin cream composition according to the present invention comprises: water, and emulsified and dispersed in the water:

(1) sodium lactate;
(2) ascorbyl palmitate;
(3) tocopheryl acetate;
(4) witch hazel;
(5) horsetail extract;
(6) a thickener component;
(7) a preservative component;
(8) a lipid-soluble component;
(9) octyl methoxycinnamate;
(10) benzophenone-3;
(11) fragrance;
(12) a complex consisting essentially of polyacrylamide, $C_{13}$–$C_{14}$ isoparaffin, laureth-7, and water; and
(13) coloring.

In this composition, the sodium lactate, the ascorbyl palmitate, the tocopheryl acetate, the witch hazel and the horsetail extract are each present in a quantity sufficient to increase the smoothness and/or firmness and to diminish the oiliness of skin to which the composition is applied.

A particularly preferred cosmetic composition of the present invention comprises: water, and emulsified and dispersed in the water:

(1) about 1.9% to about 2.6% of a stabilizer complex consisting essentially of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
(2) about 0.05% to about 0.15% of carrageenan;
(3) about 0.05% to about 0.15% of xanthan gum;
(4) about 4.25% to about 5.75% of sodium lactate;
(5) about 0.05% to about 0.15% of methylparaben;
(6) about 0.02% to about 0.1% of butylparaben;
(7) about 0.02% to about 0.1% of propylparaben;
(8) about 0.85% to about 1.15% of steareth-2;
(9) about 0.85% to about 1.15% of steareth-21;
(10) about 0.4% to about 0.6% of dimethicone;
(11) about 1.25% to about 1.75% of octyldodecyl neopentanoate;
(12) about 0.001% to about 0.02% of tocopheryl acetate;
(13) about 0.01% to about 0.03% of ascorbyl palmitate;
(14) about 3.4% to about 4.6% of octyl methoxycinnamate;
(15) about 1.7% to about 2.3% of benzophenone-3;
(16) about 6.8% to about 9.2% of witch hazel;
(17) about 0.02% to about 0.1% of horsetail extract;
(18) about 0.3% to about 0.4% of fragrance;
(19) about 4.25% to about 5.75% of a complex consisting essentially of polyacrylamide, $C_{13}$–$C_{14}$ isoparaffin, laureth-7, and water, wherein the polyacrylamide comprises from about 49.6% to about 63.8% of the complex, the $C_{13}$–$C_{14}$ isoparaffin comprises from about 21.3% to about 35.5% of the complex, the laureth-7 comprises from about 4.2% to about 11.3% of the complex, and the water comprises from about 4.2% to about 9.9% of the complex; and
(20) about 0.0001% to about 0.1% of FD&C Blue #1.

DESCRIPTION

A new combination of ingredients results in a skin cream that simultaneously promotes significant retexturizing of the skin, increasing its smoothness, improving its color, and reducing age spots, while also increasing its firmness and moisture content. The skin cream also reduces the amount of oil and/or sebum on the skins of people with oily skin.

The skin cream composition of the present invention comprises an aqueous base in which cosmetic components are emulsified and dispersed. The cosmetic components are:

(1) sodium lactate;
(2) a long-chain fatty acid ester of ascorbic acid;
(3) a short-chain carboxylic acid ester of tocopherol;
(4) witch hazel; and
(5) horsetail extract.

An optional cosmetic component is an active metabolite complex of polysaccharides and peptides extracted from a bacterial culture medium.

Preferably, the skin cream composition further comprises ancillary components. These ancillary components can include:

(1) a thickener component;
(2) a preservative component;
(3) a lipid-soluble component;
(4) a methoxycinnamate ester of a medium-chain alcohol;
(5) benzophenone-3;
(6) fragrance;
(7) a complex consisting essentially of polyacrylamide, $C_{13}$–$C_{14}$ isoparaffin, laureth-7, and water; and
(8) coloring.

Preferably, the composition includes all of these ancillary components. The ingredients are dispersed in an emulsified composition by the methods of preparation disclosed below. "Dispersed" refers to any process by which the ingredients are uniformly distributed in the emulsified base, and includes dissolving, emulsifying, and forming a colloidal suspension.

I. NATURE AND PROPORTION OF INGREDIENTS OF THE SKIN CREAM COMPOSITION

A. The Cosmetic Components

Each of the cosmetic components disclosed above contributes to the improved properties of the skin cream composition of the present invention and is present in a quantity sufficient to increase the smoothness and/or firmness, or to diminish the oiliness, of skin to which the composition is applied.

Preferred compositions for these cosmetic components are now disclosed; however, other compositions containing the required ingredients as set forth above are possible.

1. Sodium Lactate

One of the cosmetic components is sodium lactate. Preferably, the sodium lactate comprises from about 4.25% to about 5.75% of the composition. A suitable form of sodium lactate is a complex of lactic acid and sodium hydroxide in which the lactic acid comprises from about 42% to about 58% of the complex and the sodium hydroxide comprises the remainder of the complex, approximately neutralizing the lactic acid.

2. The Short-Chain Carboxylic Acid Ester of Tocopherol

Another cosmetic component is a short-chain carboxylic acid ester of tocopherol. Preferably, the short-chain carboxylic acid ester of tocopherol is selected from the group consisting of tocopheryl acetate and tocopherol propionate. Most preferably, the tocopheryl ester is tocopheryl acetate. Preferably, the tocopheryl acetate comprises from about 0.001% to about 0.02% of the composition.

3. The Long-Chain Fatty Acid Ester of Ascorbic Acid

An additional cosmetic component is a long-chain fatty acid ester of ascorbic acid. Preferably, the ascorbic acid ester is selected from the group consisting of ascorbyl palmitate, ascorbyl myristate, and ascorbyl stearate. Most preferably, the ascorbic acid ester is ascorbyl palmitate. Preferably, the ascorbic acid ester comprises from about 0.01% to about 0.03% of the composition.

4. Witch Hazel

An additional cosmetic component is witch hazel. Preferably, the witch hazel comprises from about 6.8% to about 9.2% of the composition.

5. Horsetail Extract

An additional cosmetic component is horsetail extract. Preferably, the horsetail extract comprises from about 0.02% to about 0.1% of the skin cream composition of the present invention.

6. The Active Metabolite Complex of Polysaccharides and Peptides

An additional and optional cosmetic component is an active metabolite complex of polysaccharides and peptides extracted from a bacterial culture medium. The use of this active metabolite complex is not required for the cosmetic composition of the present invention to exert its beneficial effects.

Preferably, the bacterial culture medium contains soy peptones. A suitable complex is Biodermine, available from Sederma, Le Perray en Yvelnes, France. The complex is obtained by bacterial fermentation of soy peptones (proteins, peptides, glycoproteins, and polysaccharides). The fermenter broth contains the following amino acids with levels ranging from 0.01% to 1.00%: aspartic acid, glutamic acid, serine, glycine, histidine, arginine, threonine, alanine, tyrosine, valine, methionine, isoleucine, leucine, phenylalanine, lysine, and proline. This complex stimulates immune activity, increases cell metabolism, and restores normality to the activity of the sebaceous glands in the skin, resulting in the normalization of seborrheic secretions in the skin. This reduces the amount of oil and/or sebum present on the skin and is particularly desirable to improve the complexions of people with oily skins.

B. The Ancillary Components

The ancillary components, whose use is optional but preferable, impart additional desirable properties to the skin cream composition of the present invention. These ancillary components can include:

(1) a thickener component;
(2) a preservative component;
(3) a lipid-soluble component;
(4) a methoxycinnamate ester of a medium-chain alcohol;
(5) benzophenone-3;
(6) fragrance;
(7) a complex consisting essentially of polyacrylamide, $C_{13}$–$C_{14}$ isoparaffin, laureth-7, and water; and
(8) coloring.

Preferably, the composition of the present invention comprises all the ancillary components as indicated below.

1. The Thickener Component

The thickener component can comprise at least one of xanthan gum and carrageenan. Preferably, the thickener component comprises both xanthan gum and carrageenan. Most preferably, the xanthan Bum comprises from about 0.05% to about 0.15% of the composition, and the carrageenan comprises from about 0.05% to about 0.15% of the composition.

2. The Preservative Component

The composition can further comprise a preservative component to retard microbial and mold growth in the composition, which is typically manufactured under clean but non-sterile conditions. The preservative component can comprise at least from one to four ingredients in any combination, each ingredient being selected from the group consisting of:

(1) a complex consisting essentially of propylene glycol, phenoxyethanol, chlorphenesin, and methylparaben;
(2) methylparaben;
(3) butylparaben; and
(4) propylparaben.

Preferably, the preservative component comprises all of these ingredients.

Preferably, the complex consisting essentially of propylene glycol, phenoxyethanol, chlorphenesin, and methylparaben comprises from about 1.9% to about 2.6% of the composition. Preferably, the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex. A suitable complex of propylene glycol, phenoxyethanol, chlorphenesin, and methylparaben is available as Stabilizer 388 from Lab Serobiologique, Inc., Somerville, N.J.

Preferably, the methylparaben comprises from about 0.05% to about 0.15% of the composition, the butylparaben comprises from about 0.02% to about 0.1% of the composition, and the propylparaben comprises from about 0.02% to about 0.1% of the composition.

3. The Lipid-Soluble Component

The skin cream composition of the present invention can further comprise a lipid-soluble component that provide added smoothness. The lipid-soluble component can comprise from one to four ingredients in any combination, each ingredient being selected from the group consisting of:

(1) steareth-2;
(2) steareth-21;
(3) dimethicone; and
(4) a branched-chain neopentanoate ester selected from the group consisting of octyldodecyl neopentanoate, heptyldodecyl neopentanoate, nonyldodecyl neopentanoate, octylundecyl neopentanoate, heptylundecyl neopentanoate, nonylundecyl neopentanoate, octyltridecyl neopentanoate, heptyltridecyl neopentanoate, and nonyltridecyl neopentanoate.

Preferably, the lipid-soluble component includes all of these ingredients.

Steareth-2 is polyoxyethylene (2) stearylether with 0.01% butylated hydroxyanisole and 0.005% citric acid added as preservatives. Similarly, steareth-21 is polyoxyethylene (21) stearylether with 0.01% butylated hydroxyanisole and 0.005% citric acid added as preservatives.

Most preferably, the lipid-soluble component comprises steareth-2, steareth-21, dimethicone, and octyldodecyl neopentanoate, and the steareth-2 comprises from about 0.85% to about 1.15% of the composition, the steareth-21 comprises from about 0.85% to about 1.15% of the composition, the dimethicone comprises from about 0.4% to about 0.6% of the composition, and the octyldodecyl neopentanoate comprises from about 1.25% to about 1.75% of the composition.

The Methoxycinnamate Ester of a Medium-Chain Alcohol

The composition can further comprise a methoxycinnamate ester of a medium-chain alcohol. Preferably, the methoxycinnamate ester of a medium-chain alcohol is selected from the group consisting of octyl methoxycinnamate, heptyl methoxycinnamate, and nonyl methoxycinnamate. Most preferably, the methoxycinnamate ester of the medium-chain alcohol is octyl methoxycinnamate. Preferably, the octyl methoxycinnamate comprises from about 3.4% to about 4.6% of the composition.

5. Benzophenone-3

The composition can further comprise benzophenone-3, which exerts a protective effect by screening out ultraviolet rays. Preferably, the benzophenone-3 comprises from about 1.7% to about 2.3% of the composition.

6. Fragrance

The skin cream composition of the present invention can further comprise fragrance. Preferably, the fragrance comprises from about 0.3% to about 0.4% of the composition. The fragrance used is a conventional cosmetic fragrance chosen to impart the desired olfactory properties to the skin cream composition. The use of fragrance is well-known in the cosmetic art.

The Complex of Polyacrylamide, $C_{13}$–$C_{14}$ Isoparaffin, Laureth-7, and Water The composition can further comprise a complex consisting essentially of polyacrylamide, $C_{13}$–$C_{14}$ isoparaffin, laureth-7, and water. This complex imparts desired rheological properties, namely smoothness, and bulk to the composition. Preferably, the polyacrylamide comprises from about 35% to about 45% of the complex, the $C_{13}$–$C_{14}$ isoparaffin comprises from about 15% to about 25% of the complex, the laureth-7 comprises from about 3% to about 8% of the complex, and the water comprises from about 32% to about 47% of the complex. A suitable complex is Sepigel 305, produced by Seppic S.A., Paris, France. Preferably, the complex comprises from about 4.25% to about 5.75% of the composition.

8. Coloring

The skin cream composition of the present invention can further comprise coloring to give the skin cream an aesthetically desirable appearance. Preferably, the coloring is FD&C Blue #1. Most preferably, the FD&C Blue #1 comprises from about 0.0001% to about 0.1% of the composition. The use of coloring agents is well known in the cosmetic art, and other coloring agents can be substituted for FD&C Blue #1 depending on the intended user. Many such coloring agents are available for use in cosmetic compositions.

The preferred concentrations of both the cosmetic components and the ancillary components are shown in Table I. Also shown in Table I are the mixtures of which each component is a part for the preparation of the composition as discussed below.

TABLE I

INGREDIENTS OF A PREFERRED SKIN CREAM COMPOSITION ACCORDING TO THE PRESENT INVENTION

| Mixture | Components | Percentage Range |
|---|---|---|
| I | Complex of Propylene Glycol, Phenoxyethanol, Chlorphenesin and Methylparaben[a] | 0.95–1.30 |
| II | Carrageenan | 0.05–0.15 |
| II | Xanthan Gum | 0.05–0.15 |
| III | Demineralized Water | 53.50–72.40 |
| IV | Sodium Lactate | 4.25–5.75 |
| V | Complex of Propylene Glycol, Phenoxyethanol, Chlorphenesin and Methylparaben[a] | 0.95–1.30 |
| VI | Methylparaben | 0.05–0.15 |
| VI | Butylparaben | 0.02–0.10 |
| VI | Propylparaben | 0.02–0.10 |
| VII | Steareth-2 | 0.85–1.15 |
| VII | Steareth-21 | 0.85–1.15 |
| VII | Dimethicone | 0.40–0.60 |
| VII | Octyldodecyl Neopentanoate | 1.25–1.75 |
| VII | Tocopheryl Acetate | 0.001–0.02 |
| VII | Ascorbyl Palmitate | 0.01–0.03 |
| VII | Octyl Methoxycinnamate | 3.40–4.60 |
| IX | Benzophenone-3 | 1.70–2.30 |
| X | Witch Hazel | 6.80–9.20 |
| X | Horsetail Extract | 0.02–0.10 |
| X | Active Metabolite Complex of Polysaccharides and Peptides Extracted from a Bacterial Cultural Medium[b] | 5.10–6.90 |
| XI | Fragrance | 0.30–0.40 |
| XII | Complex of Polyacrylamide, $C_{13}$–$C_{14}$ Isoparaffin, Laureth-7, and Demineralized Water | 4.25–5.75 |
| XIII | FD&C Blue #1 | 0.0001–0.10 |

[a]Complex of propylene glycol, phenoxyethanol, chlorphenesin, and methylparaben added twice; final percentage range is 1.90–2.60.
[b]Active metabolite complex is an optional ingredient.

II. PREPARATION OF THE SKIN CREAM COMPOSITION

The various mixtures and the sequence in which they are prepared and combined for the preparation in the skin cream composition of the present invention are now described in some detail. The mixtures can be combined in several orders, of which the one disclosed below is representative but not exclusive. The object of the mixing sequence is to prepare a smooth and homogeneous composition as an emulsion.

Mixtures III (demineralized water) and IV (lactic acid) are introduced into a steam jacketed stainless steel AGI kettle large enough to hold the entire preparation, and sweep mixing is begun at moderate speed while heating to 70°–75° C. This temperature and rate of mixing are maintained.

Mixtures I (the complex of propylene glycol, phenoxyethanol, chlorphenesin, and methylparaben) and II (carrageenan and xanthan gum) are introduced into another stainless steel kettle equipped with a high-speed mixer such as a Lightnin'™ Mixer. Mixtures I and II are mixed at moderate speed to form a slurry.

Next, the combination of Mixtures I and II as a slurry is added to the steam jacketed stainless steel kettle containing Mixtures III and IV at 70°–75° C. with fast sweep mixing for 5 to 10 minutes. Mixing is then reduced to moderate speed and the temperature is maintained.

Mixtures V (additional complex of propylene glycol, phenoxyethanol, chlorphenesin, and methylparaben) and VI (methylparaben, butylparaben, and propylparaben) are introduced into a third stainless steel kettle also equipped with a high-speed mixer such as a Lightnin' mixer. These components are mixed vigorously to form a slightly cloudy uniform solution.

Mixtures V and VI are then added to the kettle already containing mixtures I, II, III, and IV at 70°–75° C. with fast sweep mixing for 5–10 minutes. Mixing is then reduced to moderate speed and the temperature is maintained.

In a fourth stainless steel kettle that is steam-jacketed and equipped with a high-speed mixer such as a Lightnin' mixer, Mixtures VII (steareth-2, steareth-21, dimethicone, octyldodecyl neopentanoate, tocopheryl acetate, and ascorbyl palmitate), VIII (octyl methoxycinnamate) and IX (benzophenone-3) are combined and heated to 70°–75° C. with vigorous mixing. When Mixtures VII–IX, the oil phase, are completely liquified and uniform at 70°–75° C., they are pumped into the kettle containing Mixtures I–VI at 70°–75° C. The combination of Mixtures VII–IX and I–VI is then mixed by sweep mixing at a fast speed while also employing homogenization mixing at a fast speed for 5 to 10 minutes. The homogenization mixing is then discontinued and fast speed sweep mixing is maintained.

The batch is then cooled at a rate of 1°– C. per three minutes while maintaining mixing.

In a fifth stainless steel kettle equipped with a high speed mixer such as a Lightnin' mixer, Mixture X (witch hazel, horsetail extract, and active metabolite complex of polysaccharides and peptides, if present) is combined and mixed at moderate speed for 2–4 minutes until uniform. When the kettle containing Mixtures I–IX has cooled to 50°–55°C., Mixture X as combined is added to it. The resulting combination is mixed with sweep mixing at a fast speed for 5 to 10 minutes until homogeneous. The sequence of mixing and the steps involved in mixing are the same whether or not the active metabolite complex of polysaccharides and peptides is included.

To the combination of Mixtures I–X, Mixture XI (fragrance) is added at 50°–55° C. with sweep mixing at fast speed for 5–10 minutes until the resulting combination is homogeneous. Sweep mixing is then reduced to moderate speed.

The batch is then cooled to 40°–45° C. Mixture XII (the complex consisting essentially of polyacrylamide, $C_{14}$ isoparaffin, laureth-7, and water) is added to the batch slowly with sweep mixing at fast speed for 2–2.5 hours until uniform. Mixing is then reduced to slow sweep mixing. The batch is then cooled to 20°–25° C. with slow sweep mixing and Mixture XIII (FD&C Blue #1) is then added to impart the desired color. The final combination of Mixtures I–XIII is then filled into storage vessels for cold room storage at 18°–22° C.

ADVANTAGES OF THE INVENTION

The skin cream composition of the present invention provides significantly improved retexturization of the skin, giving significantly improved smoothness, as well as significantly minimizing age spots, improving color, together with increasing the firmness and moisture content of the skin. The skin cream of the present invention is particularly effective in improving the properties of oily skin by reducing the oil content and sebum content of the skin. This provides substantially cosmetic advantages which are not readily obtained by compositions not formulated to deal with the particular problems of oily skin.

Although the present invention has been described in considerable detail with regard to certain preferred versions thereof, other versions are possible. Therefore, the spirit and scope of the appended claims should not be limited to the descriptions of the preferred versions contained herein.

I claim:

1. A skin cream composition comprising: water, and emulsified and dispersed in the water:
   (a) sodium lactate;
   (b) a long-chain fatty acid ester of ascorbic acid selected from the group consisting of ascorbyl palmitate, ascorbyl myristate, and ascorbyl stearate;
   (c) a short-chain carboxylic acid ester of tocopherol selected from the group consisting of tocopheryl acetate and tocopheryl propionate;
   (d) witch hazel;
   (e) horsetail extract;
   (f) a methoxycinnamate ester of a medium-chain alcohol selected from the group consisting of octyl methoxycinnamate, heptyl methoxycinnamate, and nonyl methoxycinnamate;
   (g) a thickener component comprising from one to two ingredients, each ingredient being selected from the group consisting of xanthan gum and carrageenan;
   (h) a preservative component comprising from to four ingredients, each ingredient being selected from the group consisting of:
      (i) a complex of propylene glycol, phenoxyethanol, chlorphenesin, and methylparaben;
      (ii) methylparaben;
      (iii) propylparaben; and
      (iv) butylparaben;
   (i) a lipid-soluble component comprising from one to four ingredients, each ingredient being selected from the group consisting of:
      (i) steareth-2
      (ii) steareth-21;
      (iii) a neopentanoate ester of a branched-chain alcohol selected from the group consisting of octyldodecyl neopentanoate, heptyldodecyl neopentanoate, nonyldodecyl neopentanoate, octylundecyl neopentanoate, heptylundecyl neopentanoate; nonylundecyl neopentanoate, octyltridecyl neopentanoate, heptyltridecyl neopentanoate, and nonyltridecyl neopentanoate;
   (j) benzophenone-3;
   (k) fragrance;
   (l) a complex consisting essentially of polyacrylamide, $C_{13}$–$C_{14}$ isoparaffin, laureth-7, and water, wherein the polyacrylamide comprises from about 35% to about 45% of the complex, the $C_{13}$–$C_{14}$ isoparaffin comprises from about 15% to about 25% of the complex, the laureth-7 comprises from about 3% to about 8% of the water comprises from about 32% to about 47% of the complex: and (m) a coloring agent the sodium lactate, the ascorbic acid ester, the tocopherol ester, the witch hazel, and the horsetail extract each being present in a quantity sufficient to increase the smoothness or firmness and to diminish the oiliness of skin to which the composition is applied.

2. The skin cream composition of claim 1 wherein the sodium lactate comprises from about 4.25% to about 5.75% of the composition, the ascorbic acid ester comprises from about 0.01% to about 0.03% of the composition, the tocopherol ester comprises from about 0.001% to about 0.02% of the composition, the witch hazel comprises from about 6.8% to about 9.2% of the composition, and the horsetail extract comprises from about 0.02% to about 0.1% of the composition.

3. The cosmetic composition of claim 1 wherein the ascorbic acid ester is ascorbyl palmitate.

4. The cosmetic composition of claim 1 wherein the tocopherol ester is tocopheryl acetate.

5. The cosmetic composition of claim 1 wherein the thickener component comprises both xanthan gum and carrageenan, and wherein the xanthan gum comprises from about 0.05% to about 0.15% of the composition and the carrageenan comprises from about 0.05% to about 0.15% of the composition.

6. The cosmetic composition of claim 1 wherein the preservative component comprises all of:
(a) the complex of propylene glycol, phenoxyethanol, chlorphenesin, and methylparaben;
(b) methylparaben;
(c) butylparaben; and
(d) propylparaben; and wherein the complex of propylene glycol, phenoxyethanol, chlorphenesin, and methylparaben comprises from about 1.9% to about 2.6% of the composition, and methylparaben comprises from about 0.05% to about 0.15% of the composition, the butylparaben comprises from about 0.02% to about 0.1% of the composition, and the propylparaben comprises from about 0.02% to about 0.1% of the composition.

7. The cosmetic composition of claim 1 wherein the lipid-soluble component comprises steareth-2, steareth-21, octyldodecyl neopentanoate, and dimethicone, and wherein the steareth-2 comprises from about 0.85% to about 1.15% of the composition, the steareth-21 comprises from about 0.85% to about 1.15% of the composition, the octyldodecyl neopentanoate comprises from about 1.25% to about 1.75% of the composition, and the dimethicone comprises from about 0.4% to about 0.6% of the composition.

8. The cosmetic composition of claim 1 wherein the methoxycinnamate ester of the medium-chain alcohol is octyl methoxycinnamate, and wherein the octyl methoxycinnamate comprises from about 3.4% to about 4.6% of the composition.

9. The cosmetic composition of claim 1 wherein the benzophenone-3 comprises from about 1.7% to about 2.3% of the composition.

10. The cosmetic composition of claim 1 wherein the fragrance comprises from about 0.3% to about 0.4% of the composition.

11. The cosmetic composition of claim 1 wherein the complex consisting essentially of polyacrylamide, $C_{13}$–$C_{14}$ isoparaffin, laureth-7, and water comprises from about 4.25% to about 5.75% of the composition.

12. The cosmetic composition of claim 1 wherein the coloring agent is FD&C Blue #1 and the coloring agent comprises from about 0.0001% to about 0.1% of the composition.

13. A skin cream composition comprising: water, and emulsified and dispersed in the water:
(a) sodium lactate;
(b) ascorbyl palmitate;
(c) tocopheryl acetate;
(d) witch hazel;
(e) horsetail extract;
(f) a thickener component;
(g) a preservative component;
(h) a lipid-soluble component;
(i) octyl methoxycinnamate;
(j) benzophenone-3;
(k) fragrance;
(l) a complex consisting essentially of polyacrylamide, $C_{13}$–$C_{14}$ isoparaffin, laureth-7, and water; and
(m) a coloring agent; the sodium lactate, the ascorbyl palmitate, the tocopheryl acetate, the witch hazel, and the horsetail extract each being present in a quantity sufficient to increase the smoothness or firmness and to diminish the oiliness of skin to which the composition is applied.

14. The skin cream composition of claim 13 wherein the sodium lactate comprises from about 4.25% to about 5.75% of the composition, the ascorbyl palmitate comprises from about 0.01% to about 0.03% of the composition, the tocopheryl acetate comprises from about 0001% to about 0.02% of the composition, the witch hazel comprises from about 6.8% to about 9.2% of the composition, and the horsetail extract comprises from about 0.02% to about 0.1% of the composition.

15. A skin cream composition comprising: water, and emulsified and dispersed in the water:
(a) about 1.9% to about 2.6% of a stabilizer complex consisting essentially of propylene glycol, phenoxyethanol, chlorphenesin, and methylparaben, wherein the propylene glycol comprises from about 30% to about 45% of the complex, the phenoxyethanol comprises from about 22% to about 37% of the complex, the chlorphenesin comprises from about 11% to about 22% of the complex, and the methylparaben comprises from about 11% to about 22% of the complex;
(b) about 0.05% to about 0.15% of carrageenan;
(c) about 0.05% to about 0.15% of xanthan gum;
(d) about 4.25% to about 5.75% of sodium lactate;
(e) about 0.05% to about 0.15% of methylparaben;
(f) about 0 02% to about 0.1% of butylparaben;
(g) about 0 02% to about 0.1% of propylparaben;
(h) about 0 85% to about 1.15% of steareth-2;
(i) about 0 85% to about 1.15% of steareth-21;
(j) about 0 4% to about 0.6% of dimethicone;
(k) about 0 125% to about 1.75% of octyldodecyl neopentanoate;
(l) about 0.001% to about 0.02% of tocopheryl acetate;
(m) about 0.01% to about 0.03% of ascorbyl palmitate;
(n) about 3.4% to about 4.6% of octyl methoxycinnamate;

(o) about 1.7% to about 2.3% of benzophenone-3;
(p) about 6.8% to about 9.2% of witch hazel;
(q) about 0.02% to about 0.1% of horsetail extract;
(r) about 0.3% to about 0.4% of fragrance;
(s) about 4.25% to about 5.75% of a complex consisting essentially of polyacrylamide, $C_{13}$–$C_{14}$ isoparaffin, laureth-7, and water, wherein the polyacrylamide comprises from about 35% to about 45% of the complex, the $C_{13}$–$C_{14}$ isoparaffin comprises from about 15% to about 25% of the complex, the laureth-7 comprises from about 3% to about 8% of the complex, and the water comprises from about 32% to about 47% of the complex; and
(t) about 0.0001% to about 0.1% of FD&C Blue #1.

* * * * *

UNITED STATES PATENT AND TRADEMARK OFFICE
CERTIFICATE OF CORRECTION

PATENT NO. : 5,658,580
DATED : August 19, 1997
INVENTOR(S) : Mausner

It is certified that error appears in the above-identified patent and that said Letters Patent is hereby corrected as shown below:

Column 6, line 34, "Bum" should read --gum--

Column 7, lines 63, 64, "theological" should read --rhealogical--

Column 7, line 64, delete "," after the work "smoothness"

Column 8, (col. 1), line 44, "VII" should read --VIII--

Column 9, line 42, "1°-C" should read --1° C--

Column 9, line 63, "$C_{14}$" should read --$C_{13}$-$C_{14}$--

Column 11, (cl-1), lines 4, 5, insert --complex, and the-- after the word "the"

Column 12, (cl-14), line 35, "0001%" should read --0.001%--

Column 12, (cl-15), line 56, "0 02%" should read --0.02%--

Column 12, (cl-15), line 57, "0 02%" should read --0.02%--

Column 12, (cl-28), line 58, "0 85%" should read --0.85%--

UNITED STATES PATENT AND TRADEMARK OFFICE
CERTIFICATE OF CORRECTION

PATENT NO. : 5,658,580

DATED : August 19, 1997

INVENTOR(S) : Mausner

It is certified that error appears in the above-identified patent and that said Letters Patent is hereby corrected as shown below:

Column 12, (cl-28), line 59, "0 85%" should read --0.85%--

Column 12, (cl-28), line 60, "0 4" should read --0.4%--

Column 12, (cl-28), line 61, "0 125%" should read --0.125%--

Signed and Sealed this

Third Day of February, 1998

Attest:

BRUCE LEHMAN

Attesting Officer

Commissioner of Patents and Trademarks